United States Patent [19]
Gaglio et al.

[11] Patent Number: 5,326,685
[45] Date of Patent: Jul. 5, 1994

[54] VISCOUS FLUID DISPENSING APPARATUS

[76] Inventors: Thomas J. Gaglio, 4421 La Paloma; Luigi Santoriello, 3463 State St., #359, both of Santa Barbara, Calif. 93105

[21] Appl. No.: 944,303

[22] Filed: Sep. 14, 1992

Related U.S. Application Data

[63] Continuation-in-part of Ser. No. 655,137, Feb. 13, 1991, abandoned.

[51] Int. Cl.$^5$ .............................................. A61C 5/00
[52] U.S. Cl. ...................................... 433/215; 604/77
[58] Field of Search ......................... 433/80, 215, 216; 604/77; 206/63.5; 401/196

[56] References Cited

U.S. PATENT DOCUMENTS

| | | | |
|---|---|---|---|
| 3,416,527 | 12/1968 | Hoef | 604/77 |
| 4,173,219 | 11/1979 | Lentine | 604/77 |
| 4,430,013 | 2/1984 | Kaufman | 604/3 |
| 4,601,714 | 7/1986 | Burnhill | 604/286 |
| 4,665,901 | 5/1987 | Spector | 604/82 |
| 4,925,327 | 5/1990 | Wirt | 604/3 |
| 5,061,258 | 10/1991 | Martz | 604/289 |

Primary Examiner—John J. Wilson

[57] ABSTRACT

This is an applicator for applying a viscous fluid to a surface. There is a flexible backing material of a closed-cell material and a flexible dispensing material of an open-celled material disposed over and carried by the flexible backing material. The open-celled material has an internal structural spacing sized relative to the viscosity of the fluid so as to absorb and allow the fluid to slowly pass therethrough. Preferably, the flexible backing material and the flexible dispensing material are sealed together about the periphery thereof to form a hollow pocket. The fluid in the form of a gel, salve, or the like, is disposed in the hollow pocket. The pocket can be filled with an oxidizing agent and used for tooth whitening and/or gum treatment. The pocket can be attached to an adhesive backing to make adhesive bandages which apply various medications to the underlying skin area. This approach can be employed for treating wounds and blemishes. The pockets can also be used for dispensing a variety of other materials including makeup remover, moisturizer, polishes, cleansers, and the like.

16 Claims, 6 Drawing Sheets

VISCOUS FLUID DISPENSING APPARATUS

BACKGROUND OF THE INVENTION

This application is a continuation-in-part of application Ser. No. 655,137, filed Feb. 13, 1991, now abandoned.

This invention relates to applicators for applying a fluid to a surface and, more particularly, to an applicator for applying a viscous fluid to a surface comprising, a flexible backing material of a closed-cell material; and, a flexible dispensing material of an open-celled material disposed over and carried by the flexible backing material, the open-celled material having an internal structural spacing sized relative to viscosity of the fluid to absorb and allow the fluid to slowly pass therethrough. It even more specifically relates to such an applicator wherein the flexible backing material and the flexible dispensing material are sealed together about a periphery thereof forming a hollow pocket and the fluid is disposed in the hollow pocket.

There are numerous instances in which a viscous fluid such as a gel, salve, or the like, needs to be applied to a surface. These include medical, semi-medical, and non-medical uses. An example of one medical use might be the application of a medication to a wound. Semi-medical uses include such things as the treatment of acne, the whitening of tooth enamel, and the application of antiseptics to the mouth and gums. Non-medical uses include make-up removal and moisturizer application for women. Other even more non-medical uses include the application of metal polishes and the like.

Figure 1:
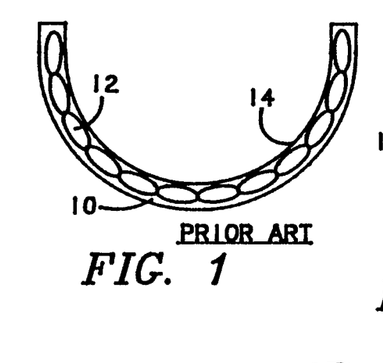
FIG. 1 is a simplified top view of a prior art trough employed by dentists for applying a tooth whitening gel to a patient's teeth.
Figure 2:
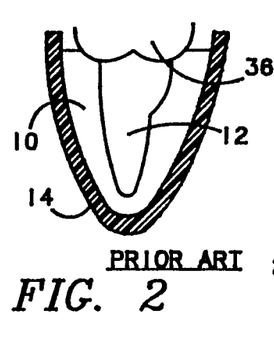
FIG. 2 is an enlarged cross section through the trough of FIG. 1 depicting how the teeth are immersed in the whitening gel therein.

The prior application of which this is a continuation in part was directed primarily to the whitening of teeth. As depicted in FIG. 1, dentists apply a whitening gel 10 containing 5% to 15% carbomide peroxide as an oxidizing (i.e. bleaching) agent to the teeth 12 of a patient by making a trough 14 of plastic to fit over the teeth 12 into which the gel 10 is placed. The teeth 12 are then inserted into the trough 14 and immersed in the gel 10 as depicted in FIGS. 1 and 2. While it is quite common to employ a 3% solution of hydrogen peroxide as a mouthwash or topical antiseptic, the higher concentrations of the oxidizing agent used in the tooth whitening gels employed by dentists have caused concern to the Federal Drug Administration (FDA) since the trough 14 method of application results in gel spill-over from the trough 14 and increased saliva excretions which then dissolve the gel 10 and cause it to move throughout the mouth and ultimately be swallowed. As can be appreciated, because of the force of gravity and the diluting effect of the saliva, the above-described approach can only be used to whiten the top teeth and is virtually useless for whitening the bottom teeth—which in may people are actually the most discolored. In other words, if the trough 14 is inverted to fit over the bottom teeth 12, the gel 10 simply runs out into the patient's mouth. As another consideration, when whitening for cosmetic reasons is the only goal of the process, it is not necessary to apply the gel 10 to the back surfaces of the teeth 12 and to the teeth 12 further back in the patient's mouth. It is only because of the trough 14 that this is done.

Figure 3:
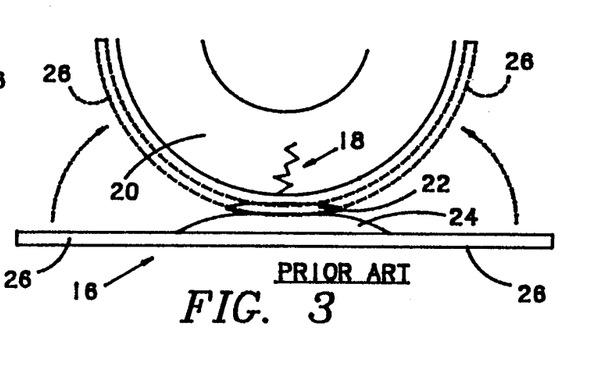
FIG. 3 is a simplified drawing showing a prior art approach to employing an antiseptic salve with an adhesive bandage.

There are also other instances where direct surface application of a gel-like material is not the most efficient or convenient way to accomplish the desired result. For example, as depicted in FIG. 3, when applying an adhesive bandage 16 to a wound 18 on a finger 20, it is generally recognized that better healing is attained and the chance of infection is reduced if an antiseptic salve 22 is put on the pad 24 (or the wound 18) before the adhesive strips 26 on opposite sides of the pad 24 are adhesively attached to the finger 20 to hold the bandage 16 in place. While this approached worked with older types of adhesive bandages wherein the adhesive strips 26 were cloth and the pad 24 was of gauze so as to contain and hold the salve 22, virtually all adhesive bandages made and sold today have plastic adhesive strips 26 and the pad 24 is covered with a plastic material which prevents the pad 24 from sticking to the wound 18. Thus, if the salve 22 is applied, it merely squirts out the sides of the adhesive bandage 16 and is lost. Forming a bandage out of gauze and adhesive tape so that the salve can be used is typically only done by professional medical people. Thus, home use normally is done with premade adhesive bandages and the salve 22 is omitted in favor of a liquid applied to the wound which quickly dries or of nothing at all. Thus, the long-term benefits of the salve 22 is lost.

What would really be of benefit in many of these various applications would be some way of dispensing the material of interest to the associated surface on a time-release basis. In other words, for example, a way of applying whitening gel to only the front surface of the top and bottom front teeth of a patient little by little over a period of time; or, of holding and slowly releasing an antiseptic fluid from an adhesive bandage pad.

Wherefore, it is an object of this invention to provide an apparatus for holding and applying viscous fluids to an associated surface of interest.

It is another object of this invention to provide an apparatus for applying viscous fluids to an associated surface of interest to be dispensed on a time-release basis.

It is still another object of this invention to provide an apparatus for applying a whitening agent to a patient's teeth in a safe and sanitary manner.

It is yet another object of this invention to provide an apparatus for applying a whitening agent to only the front surface of a patient's front teeth.

It is a further object of this invention to provide an apparatus for applying an oral antiseptic to the gums of a user on a time-release basis.

It is a still further object of this invention to provide an apparatus for applying an oral antiseptic to the gums of a user in combination with a whitening agent to the teeth.

It is another object of this invention to provide an apparatus for applying an antiseptic material to an area of a patient's skin on a time-release basis.

It is a still another object of this invention to provide an adhesive bandage for holding and applying an antiseptic material to an area of a patient's skin on a time-release basis.

Other objects and benefits of the invention will become apparent from the detailed description which follows hereinafter when taken in conjunction with the drawing figures which accompany it.

SUMMARY

The foregoing objects have been attained by the applicator of the present invention for applying a viscous fluid to a surface comprising, a flexible backing material of a closed-cell material; and, a flexible dispensing material of an open-celled material disposed over and carried by the flexible backing material, the open-celled material having an internal structural spacing sized relative to viscosity of the fluid to absorb and allow the fluid to slowly pass therethrough.

In the preferred embodiment, the flexible backing material and the flexible dispensing material are sealed together about a periphery thereof forming a hollow pocket and the fluid is disposed in the hollow pocket.

The fluid can be a glycerine-based gel. It can also contain a peroxide-based oxidizing agent. It can be an antiseptic, a makeup remover, and a skin moisturizer.

In one family of applicators, the hollow pocket is carried by adhesive-covered backing means for holding the flexible dispensing material against a surface of interest. In this group, the fluid is also disposed in the hollow pocket and can comprise a glycerine-based gel, an oxidizing agent, an antiseptic, and a time-release transdermal medication.

In one specific embodiment, the hollow pocket is sized and shaped to fit and is positioned between lips and gums/teeth of a user with the flexible dispensing material against the gums/teeth; and, the fluid contains an oxidizing agent and is disposed in the hollow pocket whereby the gums and teeth of the user are simultaneously treated by the oxidizing agent.

The hollow pocket may be filled with the material to be dispensed at the time of formation thereof. As an alternative, the internal structural spacing of the open-celled material can be chosen to be course enough to allow the fluid to be injected therethrough into the hollow pocket. As another alternative, the flexible backing material can have a slit therethrough through which the fluid can be injected into the hollow pocket followed by sealing of the slit.

DESCRIPTION OF THE PREFERRED EMBODIMENTS;

In the description which follows, the primary emphasis is on the use of the present invention for tooth whitening and periodontal purposes. Other examples of uses for the present invention are then depicted and described. As those of ordinary skill in the art will recognize and appreciate, the uses for the present invention as mentioned, shown, and described herein is not exhaustive and other uses will undoubtedly be found. It is not the intent of the inventors herein that their invention and the claims appended hereto be limited in any way by the providing of these examples. Rather, it is intended that the claims be accorded a breadth in keeping with the scope and spirit of the invention which is disclosed herein.

Figures 4, 5:
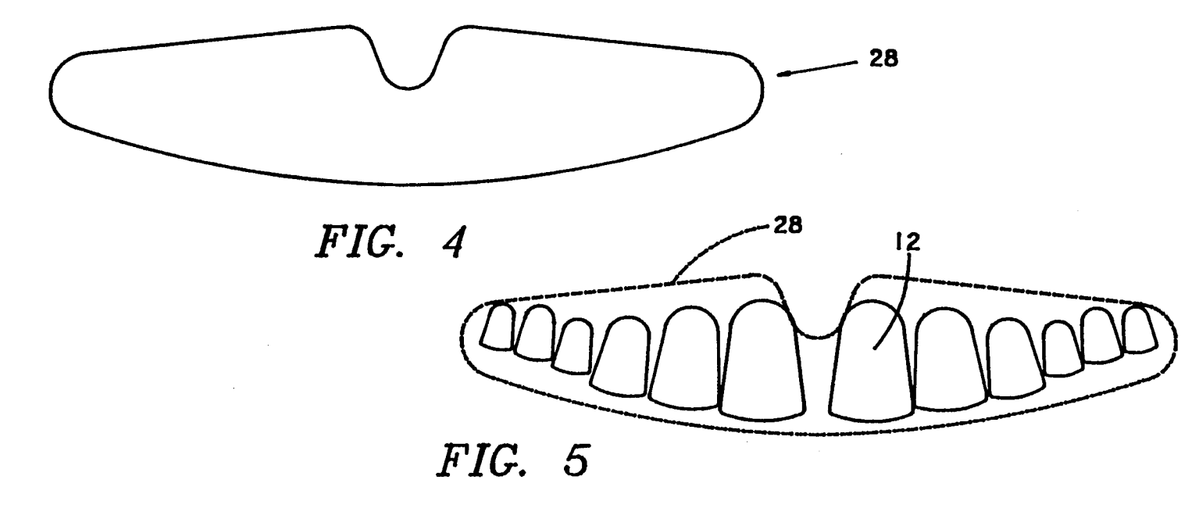
FIG. 4 is a drawing of an applicator pad according to the present invention for applying a tooth whitening gel to a patient's teeth.
FIG. 5 is a drawing of a patient's teeth showing the applicator pad of FIG. 4 ghosted as it would be positioned to apply a tooth whitening gel to the patient's teeth.
Figure 6:
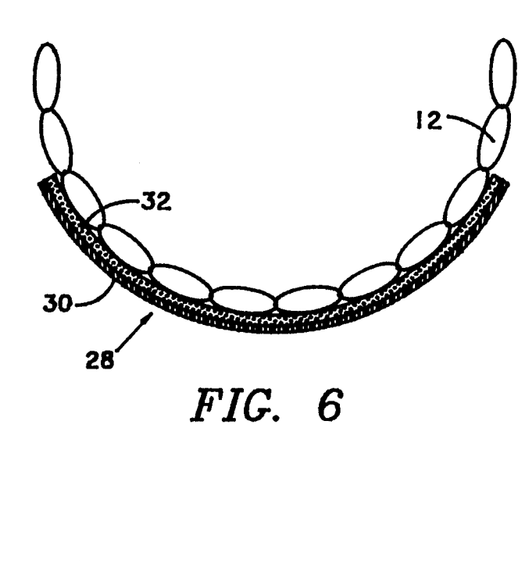
FIG. 6 is a simplified top view showing the applicator pad of FIG. 4 positioned over just the patient's front teeth.

The present invention in its most basis embodiment for tooth whitening and gum treatment purposes is depicted in FIG. 4 as an applicator pad 28. The applicator pad 28 as depicted in FIG. 4 is of a convenient design for use with the front upper teeth as depicted in FIGS. 5 and 6. The shape of the applicator pad 28 is neither critical nor a point of novelty of the present invention and different shapes can be employed which will be apparent to those of ordinary skill in the art for the particular application. As best seen from FIG. 6, the applicator pad 28 comprises a closed-cell plastic backing material 30 carrying an open-cell plastic dispensing material 32. The dispensing material 32 is placed against the surface 34 of the teeth 12 to be whitened and/or against the area of the gums 36 to be antiseptically treated.

It is worthy of note at this point with respect to the subject of oral hygiene that as mentioned earlier, hydrogen peroxide is a good oral antiseptic that is typically used in the 3% concentration solution sold over the counter. After brushing of the teeth, the hydrogen peroxide solution is typically held in the mouth and forced between and around the teeth as well as over the gums. Most people become tired of the process after a few minutes at most; so, the process is ordinarily not as effective as it might be. In its preferred embodiment, the applicator pad 28 of the present invention carries an oxidizing gel of higher concentration (e.g. 5% to 15% carbomide peroxide). Because it is comfortable and does not produce a heightened level of saliva release, it can be worn for prolonged periods. For example, after breakfast and brushing, a user can place an applicator pad 28 in the mouth on the teeth 12 during a commuting period and discard it upon arriving at work. Thus, the oxidizer has an extended period to treat the gums 36 and work its way between the teeth 12 and gums 36 for maximum effectiveness. As an ancillary benefit, the enamel of the teeth 12 is bleached and whitened. Conversely, if the user has stained teeth and employs the applicator pad 28 in the same above-described manner with tooth whitening as a primary goal, as an ancillary benefit the gums 36 receive an antiseptic and disease-fighting treatment at the same time.

Thus, regardless of the primary purpose of use, the user receives a dual benefit from the applicator pad 28 of this invention—antiseptic treatment of the gums and whitening of the teeth. This is very important as it is generally understood and agreed that as a result of the vast improvements in tooth repair and the decreases in dental caries since the introduction of fluoride in toothpaste and the like, most tooth loss is as a result of gum disease rather than from other problems. And, it is also recognized that most people do not take the time to take care of their gums to the degree that they should as it is time consuming and inconvenient. Thus, anything that makes effective treatment simple and convenient (such as the applicator pad 28 of this invention) is of extreme value in a plan of good dental hygiene. As will be recognized and appreciated from the description which follows, the applicator pad 28 of this invention can be packaged in individual foil packs for carrying in the pocket, purse, or briefcase so that good dental hygiene can be practiced throughout the day and both at home and away.

Additional benefits relative to tooth health can also be attained by employing a fluoride-containing gel 10 in the applicator pad 28. While the use of fluoride-containing toothpaste is highly beneficial, again there is the problem of getting people to use the product for long enough periods for the fluoride to penetrate the enamel and thereby strengthen it. When first employed for such purposes (i.e. before being used in toothpaste), a concentrated solution of stannis fluoride was applied to the teeth with a swab by a dentist. The patent then sat in the dental chair for a period of time sufficient for the solution to penetrate. Obviously, using the applicator pad 28 of the present invention to apply a concentrated quantity of a fluoride-containing gel 10 to the teeth for an extended period will provide superior and more instantaneous results than merely brushing with a fluoride-containing toothpaste. Those skilled in the art will also appreciate that fluoride tends to turn the enamel of the teeth a brownish color. Thus, fluoride is counter to the whitening process. On the other hand, employing a bleaching agent with the fluoride during treatment could have an offsetting end result with respect to overall tooth whiteness.

Figure 7:
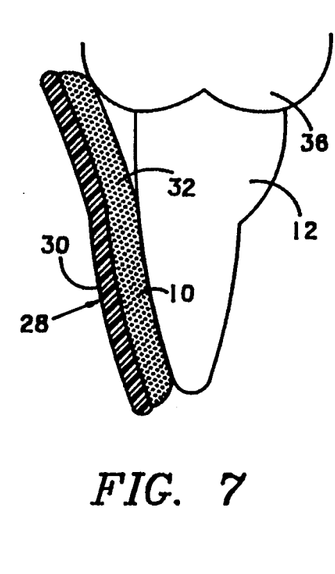
FIG. 7 is an enlarged drawing showing the applicator pad of FIG. 4 in a first embodiment.
Figure 8:
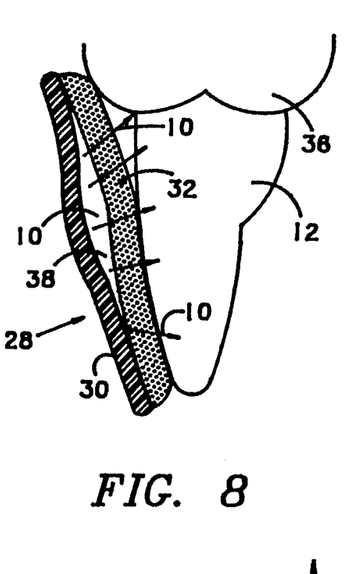
FIG. 8 is an enlarged drawing showing the applicator pad of FIG. 4 in a second and preferred time-release embodiment.

As depicted in FIG. 7, the dispensing material 32 can be carried by the entirety of the backing material 30 and the gel 10 saturated into the dispensing material 32. A preferred approach and embodiment, however, is depicted in FIG. 8. In this approach and embodiment, the dispensing material 32 is attached to the backing material 30 only about the peripheral edges forming a hollow pocket 38 or cavity in which the gel 10 is placed. Thus, the gel 10 is slowly released through the dispensing material 32 on a time-release basis. To accomplish this result in tested embodiments used for tooth applications as described above, the preferred backing material 30 comprises a closed-cell polyolefin foam sold by the Voltek division of Sekisui America Corporation of Lawrence, Mass. under the tradename VOLORA which is from 1/32" to ⅛" in thickness. The preferred dispensing material 32 comprises an open-celled polyethylene foam sold by the Sentinel Foam Products division of Packaging Industries Group, Inc. of Hyannis, Mass. under the tradename OPCELL which is from 1/16" to ⅜" in thickness.

Where peroxide antiseptic and/or bleaching agents are to be employed the preferred material is any one of several commercially available glycerine-based gels containing from 5% to 15% carbomide peroxide. In tested embodiments of the present invention employed for tooth whitening, the backing material 30 was the VOLORA material of about 1/32" thickness, the dispensing material 32 was the OPCELL material of about ⅛". The oxidizing (i.e. bleaching) gel was of 10% concentration.

Figure 9:
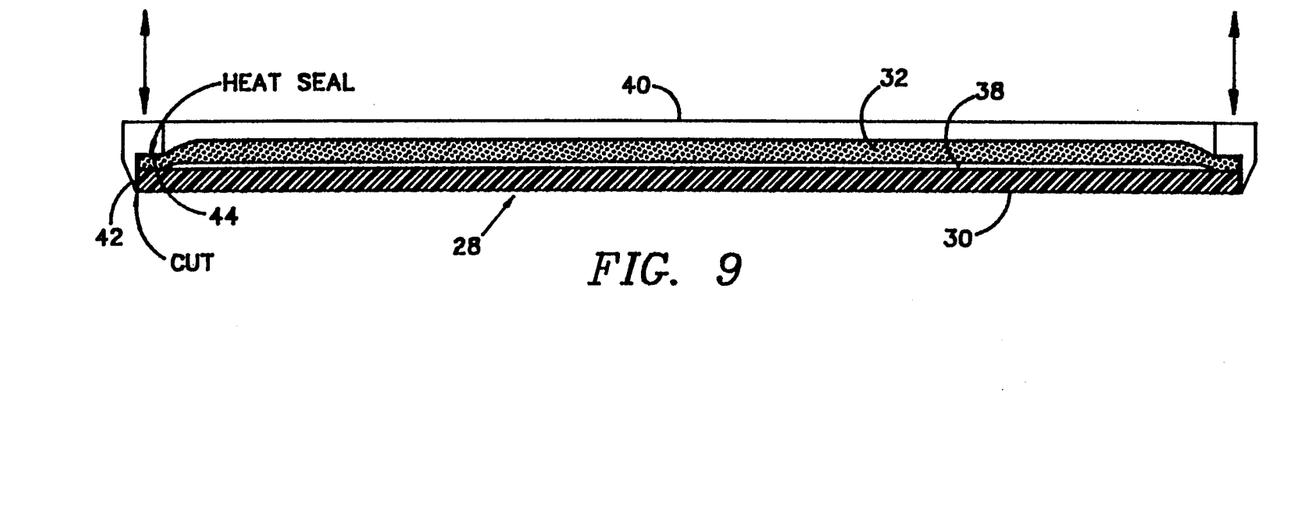
FIG. 9 is a cutaway view of the applicator pad of FIG. 4 in its embodiment of FIG. 8 depicting how the pocket shape can be cut and formed in one operation in a preferred method of manufacture.

A preferred method and apparatus for forming the pocket or hollow applicator pads 28 of FIG. 8 is depicted in FIG. 9. The dispensing material 32 is placed over the backing material 30 and then simultaneously cut and heat sealed by the cutter/sealer 40. The cutter/sealer 40 is like a cookie cutter or any other stamping cutter in that it has a peripheral shape which defines the shape of the resulting applicator pad 28. The outer periphery comprise a cutting edge 42 which cuts through the dispensing material 32 and backing material 30 when the cutter/sealer 40 is pressed into them. Just inside of the cutting edge 42 is a heated sealing surface 44 which compresses the dispensing material 32, melts it, and heat seals it to the backing material 30. The heat sealing/joining of plastics is well known in the art and, per se, forms no portion of the novelty of the present invention. Therefore, no further details of the process itself are included herein in the interest of simplicity and the avoidance of redundancy. Other well-known approaches to attaching the dispensing material 32 to the backing material 30 over the entirety or only about the periphery could, of course, be employed. The steps of this process of manufacture are depicted in FIG. 11 and the resultant gel-filled pocket 38' is depicted in FIG. 10.

Figure 10:
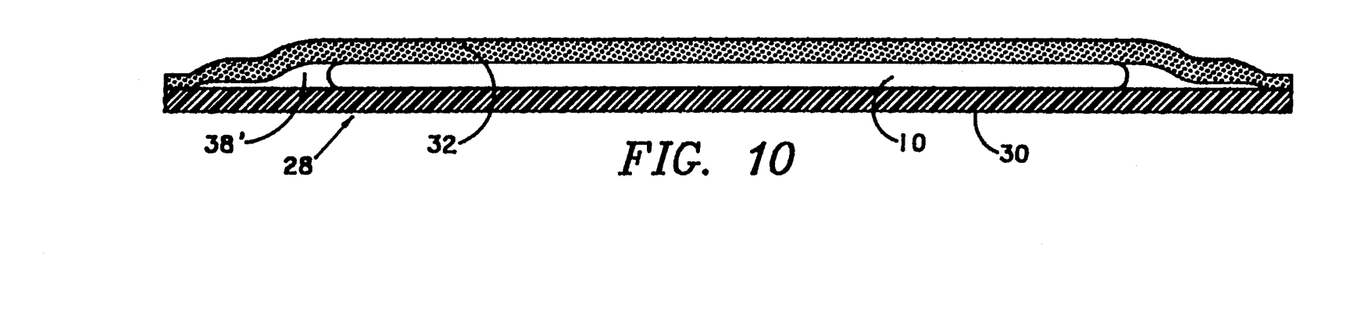
FIG. 10 is a cutaway view of the applicator pad of FIG. 9 after manufacture with a gel to be dispensed on a time-release basis contained therein.
Figure 11:
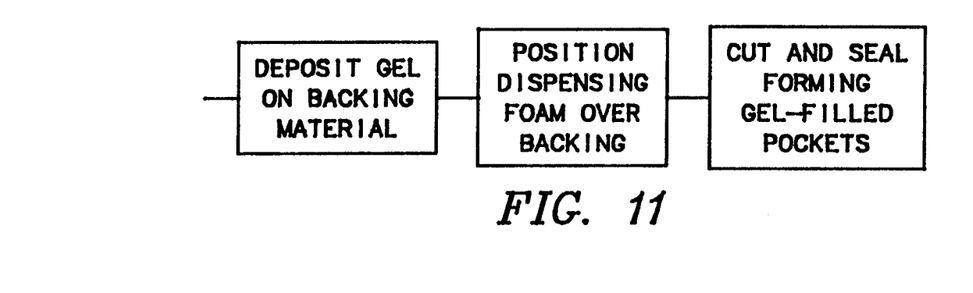
FIG. 11 is a block diagram of the steps of manufacture of the applicator pad of FIG. 10 according to one possible approach.
Figures 16, 17, 18, 19:
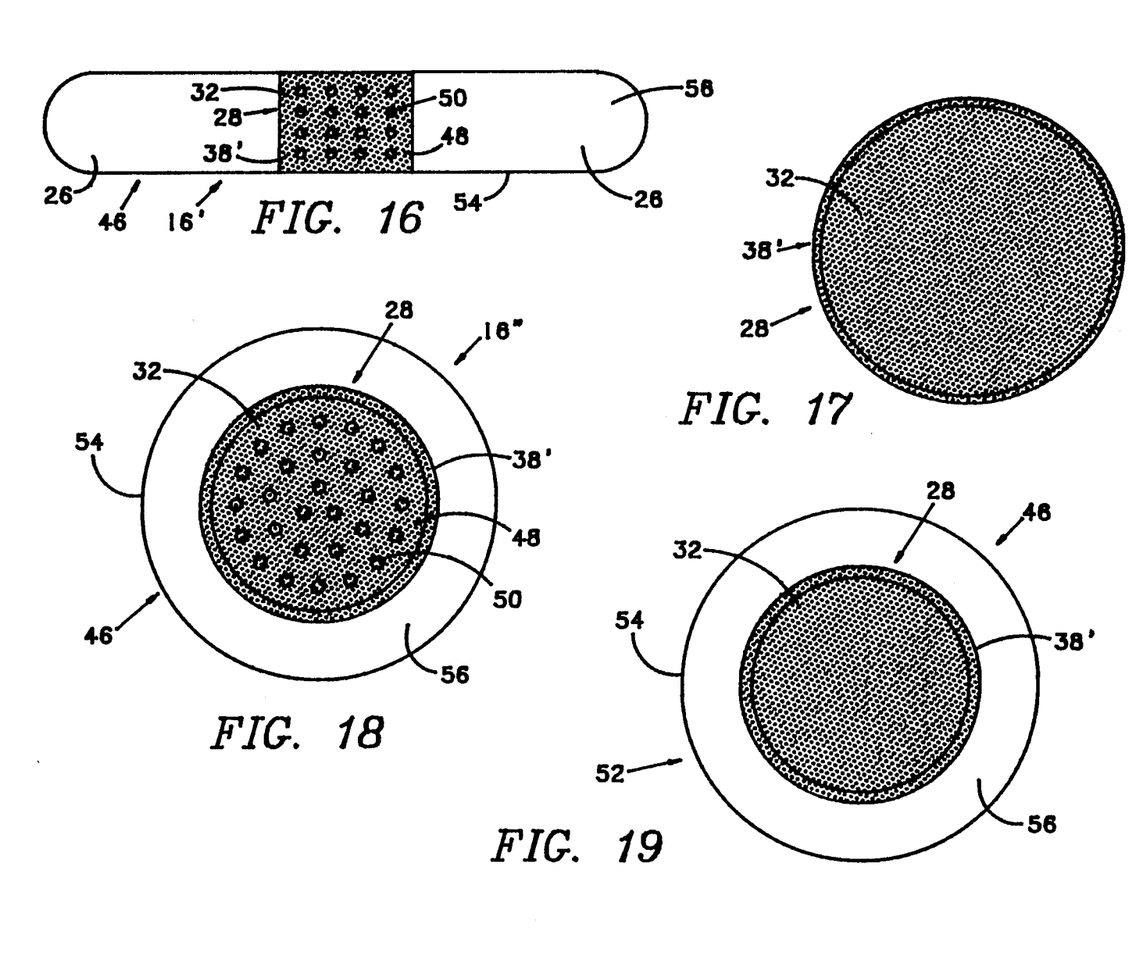
FIG. 16 is a simplified plan view of a strip adhesive bandage according to the present invention for applying an antiseptic material to an underlying area on a time-release basis wherein a non-stick surface is employed on the pad.
FIG. 17 is a simplified plan view of a circular pad according to the present invention for applying a material contained therein to an associated surface on a time-release basis.
FIG. 18 is a simplified plan view of a so-called "spot" adhesive bandage according to the present invention for applying an antiseptic material to an underlying area on a time-release basis wherein a non-stick surface is employed on the pad.
FIG. 19 is a simplified plan view of a so-called "spot" adhesive bandage according to the present invention for applying a material contained therein to an underlying area on a time-release basis wherein a non-stick surface is not employed on the pad.

The gel-filled pocket 38' of FIG. 10 can be made in various shapes and can be filled with different gels 10 for specific purposes. As described above, the gel-filled pocket 38' can be of an appropriate shape such as that of FIG. 4 and can be filled with an oxidizing gel 10 for treating the teeth 12 and gums 36 of a user in the manner described. The gel-filled pocket 38' could also be made as a small rectangle or circle (as depicted in FIG. 17) filled with the oxidizing gel 10 for treating one or two teeth 12 which are particularly discolored as in the case of a pipe smoker. The same gel-filled pocket 38' could also be reversed to place the dispensing material 32 against a cold sore or the like on the inside of the lip of the user.

The gel-filled pocket 38' could also be made as a small rectangle or circle filled with a gel 10 containing a numbing or desensitizing agent for treating one or two teeth 12 which are aching.

A larger sized rectangle or circle could be filled with other viscous fluids or gels such as the following. When filled with a cleaning agent, the gel-filled pocket 38' could be used to remove makeup, particularly eye makeup. When filled with an antiseptic astringent, the gel-filled pocket 38' could be used for deep-cleaning of the skin, particularly in the treatment of acne and the like in teenagers. The OPCELL foam makes a good non-irritating buffing foam for cleaning of the skin. Filled with moisturizer and/or wrinkle remover, a pair of the pockets 38' placed over the eyes would be beneficial in treating those areas which are so prone to wrinkling and bagging. All in all, the pockets 38' when filled with various treating agent can be employed beneficially for many makeup and beauty uses. When packaged in individual foil packs, many different products can be carried for convenient use without the necessity of carrying large containers and applicators. Foil pouches of things such as pre-moistened towelettes are, of course, known in the art; but, their uses are limited since the moistening agents are typically liquids which quite quickly evaporate and leave the user with a dry towelette. By contrast, the pre-filled pockets 38' of this invention release their contents through the cells of the dispensing material 32 and, therefore, can employ non-drying glycerine-based gels and the like as the vehicle for the active ingredients.

The pockets 38' could also be pre-filled with various convenience products such as furniture polish, auto polish, silver polish, and the like. In such case, as mentioned earlier, the most convenient method of packaging is individual foil pouches of the type well-known in the packaging art. This approach allows these convenience products to be taken along or kept in a place of convenient usage without having to carry large containers.

Figure 12:
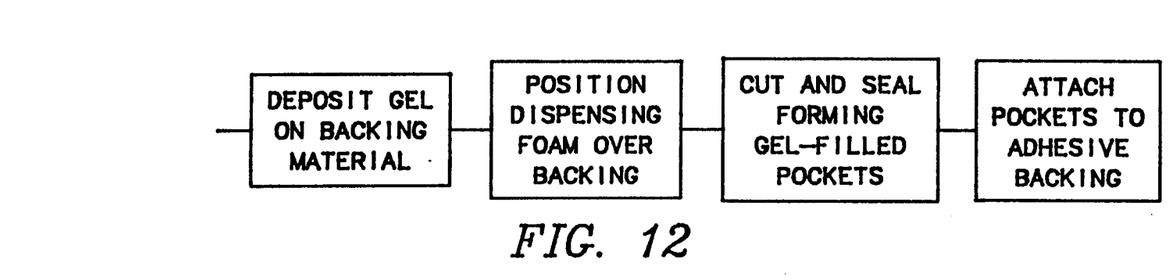
FIG. 12 is a block diagram of the steps of manufacture of the applicator pad of FIG. 10 according to the approach of FIG. 11 with the additional step of attaching the gel-filled pocket to an adhesive backing.
Figure 13:
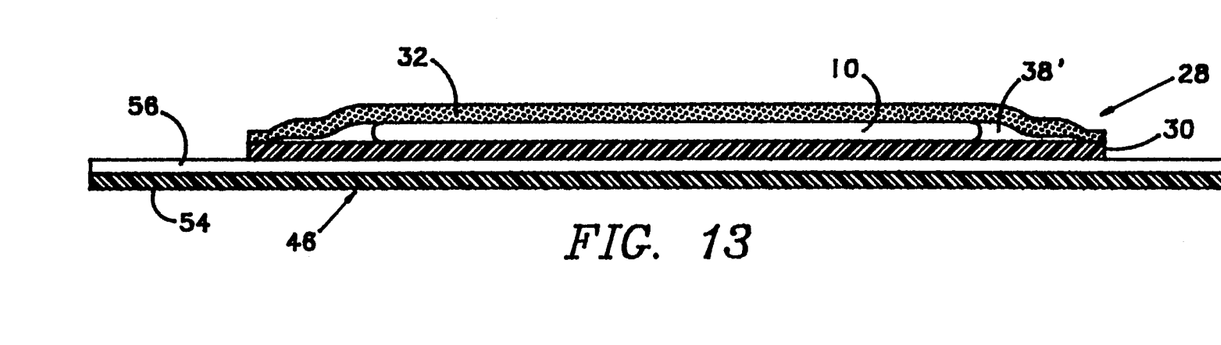
FIG. 13 is a cutaway view of an applicator pad on an adhesive backing as would be formed by the approach of FIG. 12.

In a process having steps as depicted in FIG. 12 resulting in a product as depicted in FIG. 13, the gel-filled pockets 38' can be attached to an adhesive covered backing 46 which can then used to hold the gel-filled pocket 38' over a site of interest for a particular purpose. The process of FIG. 12 comprises taking the gel-filled pocket 38' produced by the process of FIG. 11 and attaching it to the adhesive covered backing 46. Several examples of resultant products are depicted in FIGS. 16, 18, and 19. FIG. 16 depicts an adhesive bandage 16' of the strip type where the pad 24 is replaced with the gel-filled pocket 38' of the present invention wherein the gel-filled pocket 38' contains an antiseptic salve as the gel 10. To prevent the dispensing material 32 from sticking to an underlying wound, the dispensing material 32 can be covered with a plastic material 48 of the type employed in prior art adhesive bandages and wherein there are holes 50 therethrough through which the skin was allowed to "breath". In this case, the antiseptic gel 10 can move from the dispensing material 32 through the holes 50 to the wound. A so-called "spot" adhesive bandage 16" of similar construction is shown in FIG. 18.

For non-wound use, the spot applicator 52 of FIG. 19 can be employed. The applicator 52 is of similar construction to the spot adhesive bandage 16", but without the non-stick plastic material 48 over the dispensing material 32. The spot applicator 52 of FIG. 19 would be particularly useful for covering and simultaneously treating blemishes such as in the case of adolescent acne. The preferred adhesive backing 46 is of a conventional type comprising a flexible substrate 54 having an adhesive material 56 thereon. By using a flesh-colored plastic for the substrate 54, the applicator 52 would tend to hide the blemish. Using a peroxide-based oxidizing gel 10 inside the applicator 52 would provide the most effective treatment for the blemish at the same time.

With or without the non-stick plastic material 48 over the dispensing material 32, the spot applicator 52 of FIG. 19 could be employed for dispensing any time-release medication to the skin of a user. The dispensing of medication though the skin (transdermal application) over time is becoming popular in various medical treatments for which the present invention would be readily adaptable and offer possible improvements as to the types of medication which could be so dispensed.

Figure 14:
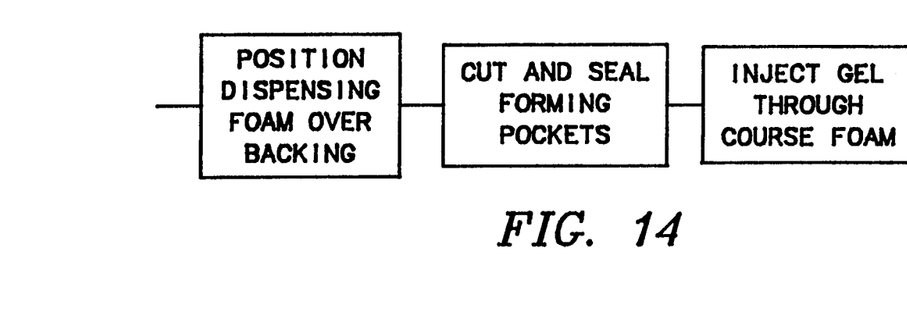
FIG. 14 is a block diagram of the steps of an applicator pad as in FIG. 10 according to a second possible approach.

While the present invention has been described to this point as a pre-filled pocket on a stand-alone basis and as attached to an adhesive backing, there are other ways in which the pocket can be made and filled. For example, rather than providing the tooth whitening version as pre-filled applicators, it may be preferable (particularly for use by dentists) to provide the whitening gel in bulk along with a supply of unfilled applicators which are then filled at the time of use. One way of accomplishing this is depicted in FIG. 14. In this case the dispensing material 32 is positioned over the backing material 30 and the materials are cut and sealed in the manner previously described to form the pockets. If a courser open-celled foam is employed, the gel 10 can be injected through the dispensing material 32 itself using a blunt hypodermic syringe type device. This merely takes a balancing of the viscosity of the gel 10 as compared with the courseness of the dispensing material 32 for the particular application. As those of ordinary skill in the art will readily recognize and appreciate, the gel 10 in each instance must be thick enough not to simply run out between of the open-cell structure of the foam and thin enough to slowly pass through over time. Obviously, if the gel 10 is too thick, it won't be lost; but, it won't be useful either. In other words, the dispensing material 32 has an internal structural spacing sized relative to the viscosity of the gel 10 such as to absorb and allow the gel 10 to slowly pass therethrough.

Figure 15:
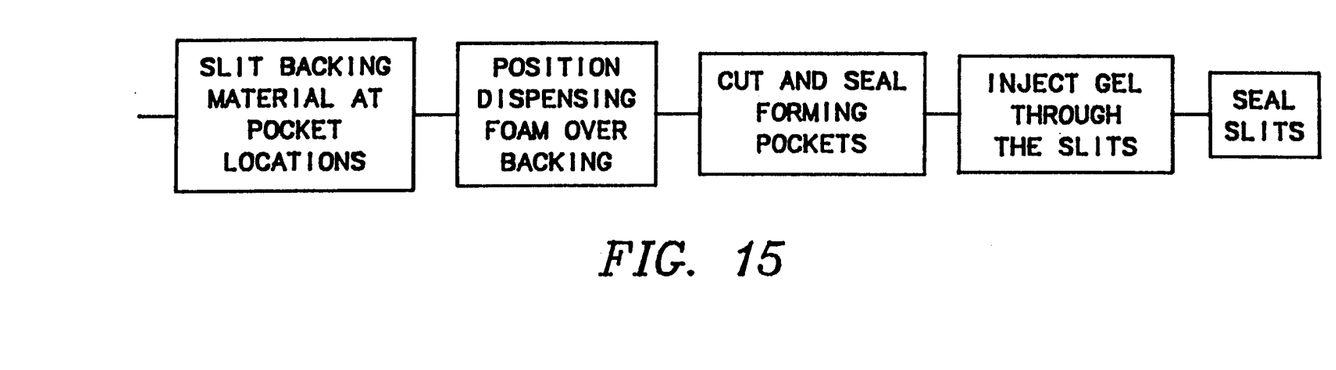
FIG. 15 is a block diagram of the steps of an applicator pad as in FIG. 10 according to a third possible approach.
Figure 20:
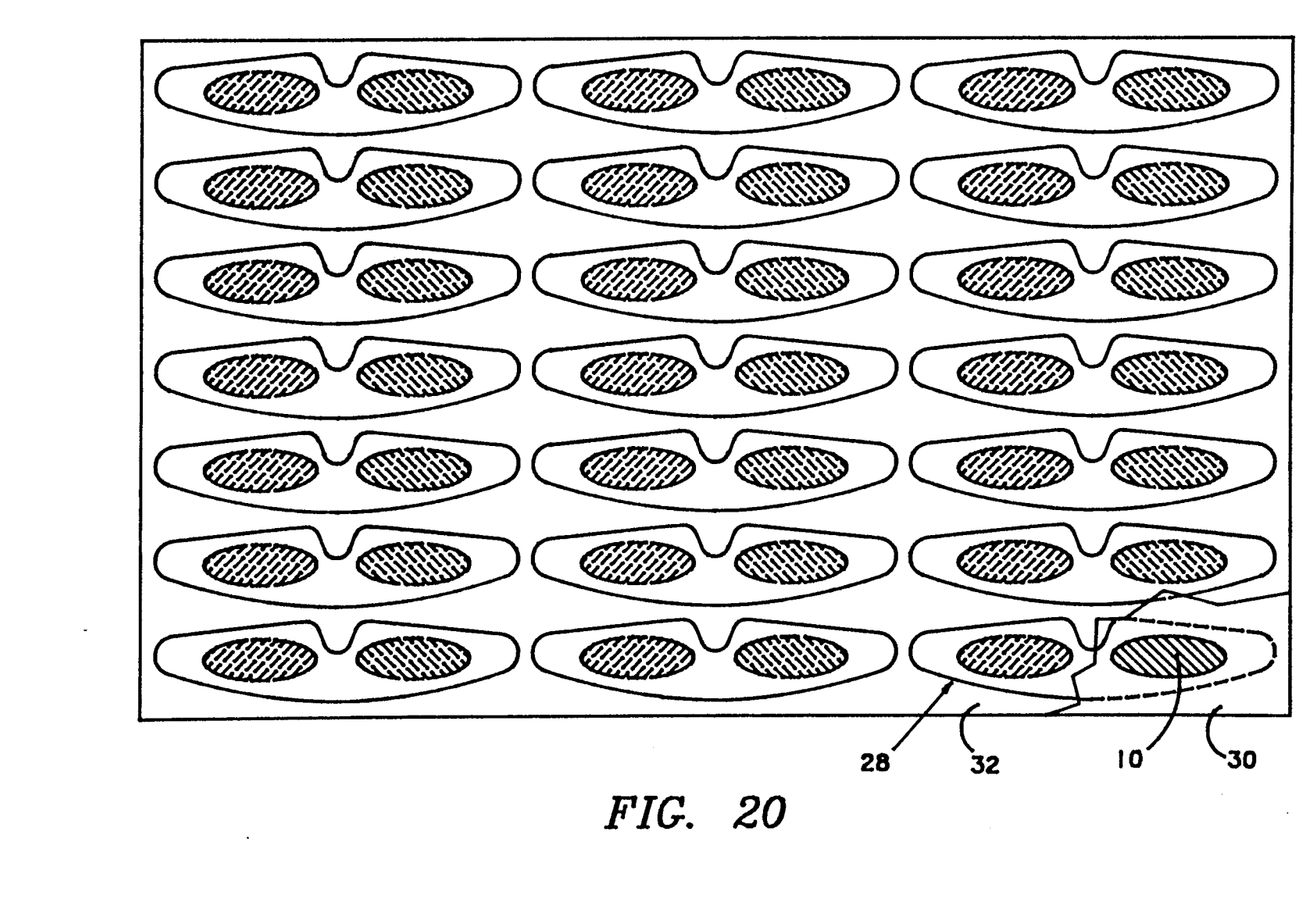
FIG. 20 is a simplified drawing depicting a preferred method of manufacture for pre-filled tooth-whitening gel applicators according to the present invention.

Another approach to the manufacture and filling of the pockets 38' is depicted in FIG. 15. In this approach, the backing material 30 is first slit at pocket locations. In this regard, the preferred method of making the pockets 38' is depicted in FIG. 20 wherein multiple pockets 38' are cut and sealed at one time. Regardless of the number of pockets 38' cut and sealed at one time, after the backing material 30 is slit the dispensing material 32 is placed over it and the pockets 38' are cut and sealed to form pockets 38' having a slit in the backing material 30 through which the gel 10 can be injected when desired through the slits. After the gel 10 has been injected into a pocket 38', the slit is then sealed. In the case of tooth whitening pockets 38', the slit can be sealed with a piece of thin plastic adhesive tape which will not interfere with the use of the pocket 38' as an applicator pad 28.

In the case of adhesive-backed pockets 38', this approach can provide an easy method of manufacture on an automated basis. The backing material 30 could be slit at first station and then the pockets 38' formed at a second station. The pockets 38' could then be filled though the slit at a third station and then the filled pockets 38' applied to the adhesive backing 46 thereby simultaneously sealing the slit at a fourth station.

Thus, it can be seen that the present invention can be employed to advantage in many ways to accomplish a variety of different objectives not attainable with any prior art devices.

Wherefore, having thus described the present invention,

What is claimed is:

1. An applicator for applying a viscous fluid to a surface of a human body on a time-release basis comprising:
   a) a flexible backing material of a closed-cell material; and,
   b) a flexible dispensing material of an open-celled material disposed over and carried by said flexible backing material, said open-celled material having an internal structural spacing sized relative to viscosity of the fluid to absorb and allow the fluid to slowly pass therethrough; wherein,
   c) said flexible backing material and said flexible dispensing material are sealed together about a periphery thereof forming a hollow pocket and the fluid is disposed in said hollow pocket.

2. The applicator of claim 1 wherein:
the fluid is a glycerine-based gel.

3. The applicator of claim 1 wherein:
the fluid contains a peroxide-based oxidizing agent.

4. The applicator of claim 1 wherein:
the fluid is an antiseptic.

5. The applicator of claim 1 wherein:
the fluid is a makeup remover.

6. The applicator of claim 1 wherein:
the fluid is a skin moisturizer.

7. The applicator of claim 1 wherein:
said hollow pocket is carried by adhesive-covered backing means for holding said flexible dispensing material against a skin surface of interest.

8. The applicator of claim 7 wherein:
the fluid is a time-release transdermal mediation.

9. The applicator of claim 1 wherein:
   a) said hollow pocket is sized and shaped for positioning between lips and ums/teeth of a user with said flexible dispensing material against said gums/teeth; and,
   b) the fluid contains an oxidizing agent and is disposed in said hollow pocket whereby gums and teeth of said user are simultaneously treated by said oxidizing agent.

10. An applicator for applying a viscous medication to the skin of a user on a time-release basis comprising:
    a) a flexible backing material of a closed-cell material;
    b) a flexible dispensing material of an open-celled material disposed over and carried by said flexible backing material, said open-celled material having an internal structural spacing sized relative to viscosity of the medication to absorb and allow the medication to slowly pass therethrough on a time-release basis, said flexible backing material and said flexible dispensing material being sealed together about a periphery thereof forming a hollow pocket, the medication being disposed in said hollow pocket; and,
    c) adhesive-covered backing means carrying said hollow pocket for holding said flexible dispensing material against the skin of the user at a location of interest, said adhesive-covered backing means comprising a flexible substrate carrying an adhesive material thereon.

11. The applicator of claim 10 wherein:
the medication is a glycerine-based gel containing a peroxide-based oxidizing agent.

12. The applicator of claim 10 wherein:
the medication is an antiseptic.

13. The applicator of claim 10 wherein:
the medication is a time-release transdermal medication.

14. An applicator for applying an oxidizing agent on a time-release basis to teeth and the gums of a user comprising:
    a) a flexible backing material of a closed-cell material;
    b) a flexible dispensing material of an open-celled material disposed over and carried by said flexible backing material, said flexible backing material and said flexible dispensing material being sealed together about a periphery thereof forming a hollow pocket, said hollow pocket being sized and shaped for positioning between the lips and the teeth/gums of the user with said flexible dispensing material against said teeth/gums; and,
    c) a viscous oxidizing agent containing an oxidizing agent disposed in said hollow pocket, said open-celled material having an internal structural spacing sized relative to the viscosity of the oxidizing agent allowing the oxidizing agent to slowly pass through said open-celled material on a time-release basis whereby the teeth and gums of the user are simultaneously treated by said oxidizing agent.

15. The applicator of claim 14 wherein:
    a) said closed-cell material of said flexible backing material is a closed-cell polyolefin foam being from 1/32" to ⅛" in thickness;
    b) said open-celled material of said flexible dispensing material is an open-celled polyethylene foam being from 1/16" to ⅜" in thickness; and,
    c) said oxidizing agent is a glycerine-based gel containing from 5% to 15% carbomide peroxide.

16. The applicator of claim 15 wherein:
    a) said closed-cell polyolefin foam is about 1/32" in thickness;
    b) said open-celled polyethylene foam is about ⅛" in thickness; and,
    c) said oxidizing agent contains 10% carbomide peroxide.

* * * * *